United States Patent [19]

Bonnet et al.

[11] Patent Number: 5,540,726
[45] Date of Patent: Jul. 30, 1996

[54] SUPRAVENTRICULAR TACHYCARDIA DETECTION APPARATUS AND METHODS

[75] Inventors: Jean-Luc Bonnet, Vanves; Anne Bouhour, Paris, both of France

[73] Assignee: Ela Medical S.A., Montrouge, France

[21] Appl. No.: 363,738

[22] Filed: Dec. 23, 1994

[30] Foreign Application Priority Data

Dec. 31, 1993 [FR] France ................ 93 15939

[51] Int. Cl.$^6$ ..................... A61N 1/365
[52] U.S. Cl. ........................... 607/14
[58] Field of Search ............... 607/14, 17, 18, 607/19, 20

[56] References Cited

U.S. PATENT DOCUMENTS 4,932,406 6/1990 Berkovitz.
5,271,394 12/1993 Girodo et al. ............... 607/15

FOREIGN PATENT DOCUMENTS

| | | |
|---|---|---|
| 360668 | 9/1989 | European Pat. Off. . |
| 448193 | 1/1991 | European Pat. Off. . |
| 488841 | 11/1991 | European Pat. Off. . |
| 559193 | 3/1993 | European Pat. Off. . |
| 2544989 | 4/1983 | France . |

Primary Examiner—William E. Kamm
Assistant Examiner—Scott M. Getzon
Attorney, Agent, or Firm—Orrick Herrington & Sutcliffe

[57] ABSTRACT

A process and device to control a cardiac pacemaker enslaved to at least one physiological parameter. The pacemaker also possesses a mode of desynchronization of the ventricular stimulation when the atrial rhythm is too rapid for synchronous operation. One compares a detected coupling interval (PP) with an escape interval calculated by the enslavement ($EI_{ASSERV}$). The calculated enslavement escape interval is preferably decreased by a prematurity factor (x), for example, 0 to 50%, preferably approximately 37.5%, of the calculated escape interval. After the comparison, one counts the number of cardiac cycles for which the coupling interval detected is less than the calculated escape interval, and one triggers the mode of desynchronization (FALLBACK) when the count exceeds a given threshold (y), for example 50 to 75%, preferably approximately 75% of the total number (N) of cardiac cycles analyzed.

43 Claims, 1 Drawing Sheet

5,540,726

SUPRAVENTRICULAR TACHYCARDIA DETECTION APPARATUS AND METHODS

The invention concerns active implantable medical devices, more particularly devices including a cardiac stimulation function (such as pacemakers) in which the stimulation frequency is enslaved to a physiological parameter, i.e., a rate adaptive pacemaker.

BACKGROUND OF THE INVENTION

Cardiac pacemakers known as "double chamber" pacemakers have a function, among others, to follow the spontaneous cardiac rhythm detected at the level of the atrium (referred to as the "atrial rhythm" or the "atrial frequency"), and to stimulate the ventricle in synchronism with the detected atrial rhythm. Nevertheless, this synchronization presents an upper rate limit known as the "maximal frequency of ventricular stimulation". If the patient develops a crisis of atrial tachycardia (also called a supraventricular tachycardia or "SVT"), then it is necessary to limit the ventricular synchronization to a controlled or defined range. This is to avoid stimulating the ventricle too rapidly, beyond a maximal frequency acceptable to the individual.

Several solutions have been implemented to control the ventricular stimulation frequency in the case of such a detected excessive acceleration of the atrial frequency. All these devices have for an object to try to keep a certain synchronization beyond the maximal frequency and, if the atrial frequency continues to exceed the maximal ventricular synchronization frequency, they begin to operate in a mode of asynchronous stimulation, tending to reduce the ventricular stimulation frequency to a lower and more tolerable ventricular frequency. Then, as soon as the atrial frequency falls below the maximal synchronization limit, a phase of progressive re-synchronization is started.

FR-A-2 544 989 refers to a process of ventricular synchronization for a sensed atrial frequency that is above the maximal ventricular synchronization frequency, by lengthening the atrial-ventricular delay (A-V delay) for a first atrial frequency range, so as not to sense (i.e., to skip) a selected atrial signal among a sequence of atrial signals, in the elevated frequency range. If these conditions persist, then the ventricular stimulation is desynchronized from the sensed atrial frequency, and decreased until a base frequency is reached. This mode of functioning is called "fallback".

U.S. Pat. No. 4,932,046 follows in many respects the same idea. It differs, however, in that the desynchronization occurs immediately, i.e., as soon as the atrial frequency goes above the maximal ventricular synchronization frequency, and the ventricular frequency then changes to a frequency which is indicated by a physiological sensor.

EP-A-0 448 193 presents yet a different approach of the problem. The information delivered by the physiological sensor serves to determine the maximal ventricular synchronization frequency. The desynchronization of the ventricular stimulation from the atrial frequency is to a frequency corresponding to that indicated by the sensor. The desynchronization is realized in a similar manner as described in the preceding cases.

In all these proposals of the prior art, the information of the physiological sensor is, however, used only after desynchronization, for the adjustment of the ventricular frequency in connection with the fallback phase. In no case, however, is the information provided by the sensor used to establish and confirm the onset of a pathological acceleration of the atrium.

SUMMARY OF THE INVENTION

It is an object of the present invention to use the information of a physiological sensor to detect and confirm the presence of a supra-ventricular tachycardia (SVT), and in response to trigger a phase of desynchronization, followed, if necessary, by a phase of "fallback."

Another object of the invention is to fill in for absences of detection in case of atrial fibrillation, in a manner sufficient to confirm the necessity of a desynchronization and possibly of a "fallback."

Broadly, the present invention is directed to an apparatus and a process of controlling a cardiac pacemaker having an operating mode in which a stimulation frequency is enslaved to (i.e., determined as a function of) at least one physiological parameter, and possessing a mode of desynchronization of the ventricular stimulation when the atrial rhythm is too rapid for tolerable synchronous operation, in which the desynchronization mode is triggered in response to a comparison of a detected coupling interval with an escape interval calculated by the enslavement (i.e., the escape interval is calculated as a function of the sensed physiological parameter). The escape interval is the inverse of the stimulation frequency, usually expressed in milliseconds.

In a preferred embodiment, the aforementioned comparison is of, on the one hand, the detected coupling interval, and, on the other hand, the escape interval calculated by the enslavement and decreased by a factor of prematurity. The prematurity factor may be expressed in the form a programmable percentage of the escape interval calculated by the enslavement. The percentage may be set, for example, between 0 and 50%, preferably approximately 37.5%. Alternately, the prematurity factor may be a programmable delay interval, for example, a delay period in the range of between 50 and 300 ms, preferably on the order of 150 ms.

The present invention also includes, after having compared the detected coupling interval with the escape interval calculated by the enslavement, counting the relative number of cardiac cycles, for a sample of N cardiac cycles, in which the detected coupling interval is less than the escape interval calculated by the enslavement, and triggering (i.e., initiating) the desynchronization mode when the count value exceeds a given threshold. The threshold is preferably expressed in the form of a programmable percentage of a first number N of analyzed cardiac cycles (for example, a percentage selected from between 50 and 75%, preferably on the order of 75%). Alternatively, the threshold is in the form of a programmable number of cardiac cycles (for example, a number selected from between 10 and 255, preferably on order of 100).

The invention is particularly applicable for use in a cardiac pacemaker capable of at least sensing atrial or ventricular events and stimulating the ventricle in synchronism with the sensed atrial rhythm.

BRIEF DESCRIPTION OF THE DRAWINGS

Further features of the invention, its nature and various advantages, will be more apparent from the accompany drawing and the following detailed description of the invention in which the FIGURE shows a method in accordance with a preferred embodiment of the invention.

DETAILED DESCRIPTION OF THE INVENTION

Figure 1:
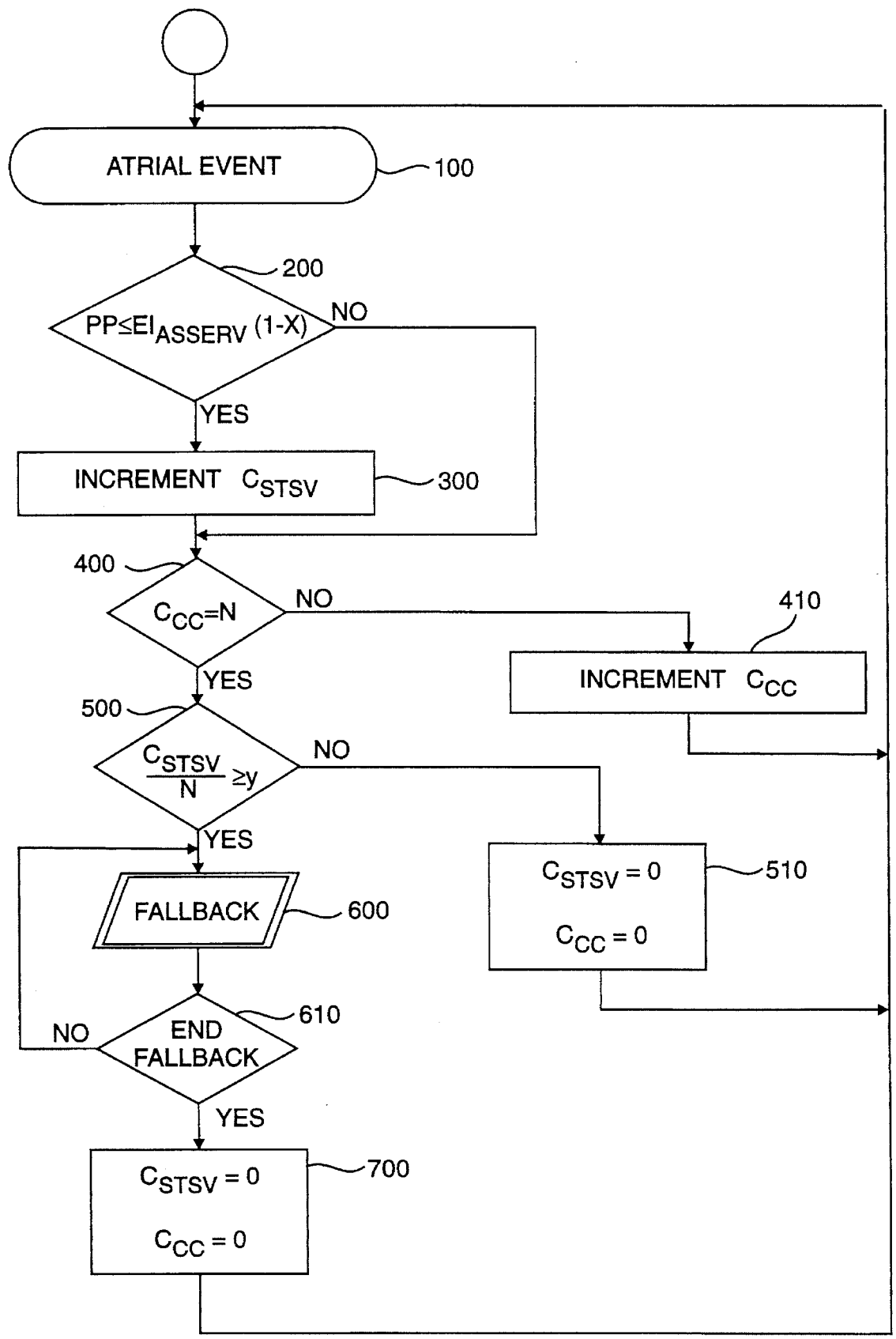

With reference to the FIGURE, a method of the present invention is illustrated. It is noted that the illustrated algorithm, and therefore the process of the invention, can be advantageously implemented by appropriately programming a microprocessor of the implantable device, or with the help of equivalent dedicated solid state circuits. The design and construction of such a software and/or hardware implemented construction is within the abilities of a person of ordinary skill in the art, and will not be described more in detail for this reason. Furthermore, this algorithm is designed to be implemented when the physiological sensor (or at least one of physiological sensors) is related to the patient's activity (cardiac output requirements) and the "fallback" function is present and has been enabled by programming.

The atrial rhythm is monitored, both when it is spontaneous ("sensed") and stimulated ("paced"). The time interval between two consecutive atrial beat events, i.e., the cardiac cycle, whether spontaneous or stimulated, called the "coupling interval" or "interval PP", is measured. A coupling interval is determined for each atrial beat, and the determined interval is updated in an appropriate manner in a memory or a counter of the implanted device.

The implanted device also includes a circuit of enslavement, operating in response to a sensed parameter produced by a physiological parameter sensor (which may be one or more various physiological sensors). This circuit calculates and delivers a control signal, called "escape interval of enslavement" (herein called "$EI_{ASSERV}$"), that will be used to determine the ventricular stimulation frequency when the device is operating in the enslaved or rate responsive mode. The implanted device also includes a first counter indicating a total number of analyzed cardiac cycles (herein referred to as "$C_{CC}$"). A second counter also may be included that counts a number of cycles that is called "cycles in suspicion of SVT" (herein referred to as "$C_{SSTV}$"), which is defined as being cycles when the coupling interval PP is shorter than a value equal to the escape interval of enslavement $EI_{ASSERV}$ (a control value) decreased by a given quantity or proportion that is the "prematurity factor." In the example described, the prematurity factor is defined as a percentage x of the escape interval of enslavement $EI_{ASSERV}$; but this choice is not limiting, and could also be expressed in absolute form by programming a time duration value.

Broadly, the process of the invention concerns an examination of a sequence of N cardiac cycles and, if during these N cycles the number of cycles in suspicion of SVT reaches a programmable percentage of the total number of cycles of the sequence, it is considered that there is an effective presence an SVT. As a result, a fallback mode is engaged. At the end of the fallback mode, an asynchronous pacing mode may be used, such as a fixed or an enslaved pacing rate, which forms no part of the present invention.

With reference to the algorithm illustrated the FIGURE, the process begins at step 100, when an atrial beat event is detected (either sensed or paced). At the step 200, the coupling interval PP of this event is compared to the escape interval of enslavement $EI_{ASSERV}$, which is determined from the physiological parameter sensed by a physiologic sensor, decreased by the prematurity factor x.

If the coupling interval PP is less than this term, which means that the atrial frequency is clearly greater than the control frequency delivered by the physiologic sensor (at step 300), the cycles in suspicion of SVT counter $C_{SSTV}$ is incremented. The routine then passes to step 400. In the case that the interval PP is not less than the term, the routine passes directly to the step 400.

At step 400, the count of the cardiac cycles $C_{CC}$ is compared to a predetermined limit N, corresponding to the duration of the analysis sequence in terms of the number of cycles analyzed. If this limit N is not reached, the counter $C_{CC}$ is incremented (step 410), and the device returns to wait for the next atrial event at step 100. If on the other hand counter $C_{CC}$ has reached the limit N, then at step 500, the proportion of the number of cycles in suspicion of SVT is compared to the total number of cycles N in the form of a fraction. If this fraction is less than a programmable value y, it is considered that there is no proven SVT, and at step 510 the two counters $C_{SSTV}$ and $C_{CC}$ are re-initialized (i.e., reset to zero). The routine then returns to wait for a new atrial event, at step 100.

If on the other hand, the fraction is greater than or equal to y, that is to say a great number of suspicious cycles among the N cycles is found, then it is considered (determined) that there has been an effective onset of an SVT and, correspondingly, the fallback mode is triggered (step 600).

The fallback mode is well known in the art, for example, as described in the publications discussed at the beginning of the description, and accordingly is not described here in detail.

When the fallback mode comes to an end (tested at step 610, e.g., for the atrial rate falling below the maximum rate), one re-initializes counters $C_{SSTV}$ and $C_{CC}$ at step 700 and returns to wait for a new atrial event at step 100. It is apparent that the control information of escape interval $EI_{ASSERV}$, that is derived of one or several physiological parameters measured by one or more sensors, serves to determine whether or not to trigger the fallback mode. It is, therefore, a characteristic of the invention, that the test can be implemented each time before fallback is to be instituted. It is also apparent that the present invention can equally serve, in a manner itself known, functions to control the process of the subsequent fallback by acting on the system of enslavement operating under control of the one or more sensors. It is noted that, although the above-mentioned example referred to comparisons using values of percentage (such as x and y), it also is within the scope of the invention to use absolute values, such as a duration or number of cycles, respectively instead of percentage values. Similarly, some programmable values could be determined and fixed in advance by programming. Set forth below is a table giving examples of programmable values that are foreseeable for an implementation of the invention.

TABLE

|  | Range | Nominal |
| --- | --- | --- |
| x (prematurity factor) | 0 to 50% | 37.5% |
| N (number of analyzed cycles) | 10 to 256 | 256 |
| y (threshold of suspicion of SVT) | 50 to 75% | 75% |

One of ordinary skill in the art will appreciate that the present invention can be practiced other than by the foregoing embodiments, which are presented for purposes of illustration, and not of limitation.

We claim:

1. A process of controlling a cardiac pacemaker having an enslavement to at least one physiological parameter and possessing a mode of desynchronization of the ventricular stimulation when the atrial rhythm is too rapid, wherein the improvement comprises triggering the mode of desynchronization (FALLBACK) in response to a comparison of the coupling interval detected (PP) with the escape interval calculated by the enslavement (EI$_{ASSERV}$).

2. The process of claim 1, in which the said comparison comprises the step of comparing the coupling interval detected and the escape interval calculated by the enslavement decreased by a prematurity factor.

3. The process of claim 2, in which the prematurity factor is expressed in the form of a programmable percentage (x) of the escape interval calculated by the enslavement.

4. The process of claim 3, in which the programmable percentage of the escape interval calculated by the enslavement is comprised between 0 and 50%, preferably approximately 37.5%.

5. The process of claim 2, in which the prematurity factor is expressed in the form of a programmable duration.

6. The process of claim 5, in which the programmable duration is comprised between 50 and 300 ms, preferably approximately 150 ms.

7. The process of claim 1, in which, after having compared the coupling interval detected with the escape interval calculated by the enslavement, one counts the number of cardiac cycles in which the coupling interval detected is less than this calculated escape interval and one triggers the mode of desynchronization when the corresponding count ($C_{SSTV}$) exceeds a given threshold.

8. The process of claim 7, in which the given threshold is expressed in the form of a programmable percentage (y) of the total number (N) of cardiac cycles analyzed.

9. The process of claim 8, in which the programmable percentage of the total number of analyzed cardiac cycles is comprised between 50 and 75%, preferably approximately 75%.

10. The process of claim 7, in which the given threshold is expressed in the form of a programmable number of cycles.

11. The process of claim 10, in which the programmable number of cycles is comprised between 10 and 255, preferably approximately 100.

12. A cardiac pacemaker having an enslavement to at least one physiological parameter, an enslavement escape interval that is a function of the physiological parameter, and means (FALLBACK) for desynchronization of the ventricular stimulation when the atrial rhythm is too rapid, comprising means to detect a coupling interval, means to compare the coupling interval detected (PP) with the enslavement escape interval (EI$_{ASSERV}$), and to trigger the means for desynchronization in response to this comparison.

13. The cardiac pacemaker of claim 12, comprising a means for counting the number of cardiac cycles in which the coupling interval detected is less than the escape interval and to trigger the means for desynchronization when the value of corresponding count exceeds a predetermined threshold.

14. A process of controlling a cardiac pacemaker having a sensor to detect at least one physiological parameter, a mode of synchronization of the ventricle stimulation to the atrial rhythm, and a mode of desynchronization of the ventricular stimulation to the atrial rhythm when the atrial rhythm is too rapid, comprising the steps of:

a) sensing atrial events;

b) determining a coupling interval between successive atrial events;

c) determining an escape interval of enslavement calculated as a function of the at least one sensed physiological parameter;

d) comparing the determined coupling interval to the calculated enslavement escape interval; and e) triggering operation in the desynchronization mode as a function of said comparison.

15. The process of claim 14 wherein step d) further comprises providing a prematurity factor, decreasing the calculated enslavement escape interval by the prematurity factor, and comparing the determined coupling interval to the decreased calculated enslavement escape interval.

16. The process of claim 15 wherein providing the prematurity factor further comprises providing a percentage of the calculated enslavement escape interval.

17. The process of claim 15 wherein providing the prematurity factor further comprises providing a percentage of the calculated enslavement escape interval selected from between 0 and 50%.

18. The process of claim 15 wherein providing the prematurity factor further comprises providing a percentage of approximately 37.5% of the calculated enslavement escape interval.

19. The process of claim 15 wherein providing the prematurity factor further comprises providing a programmable duration.

20. The process of claim 15 wherein providing the prematurity factor further comprises providing a programmable duration selected from between 50 and 300 ms.

21. The process of claim 15 wherein providing the prematurity factor further comprises providing a programmable duration of approximately 150 ms.

22. The process of claim 14 wherein step d) further comprises counting the number of cardiac cycles in which the determined coupling interval is less than the calculated escape interval, and step e) further comprises triggering the operation in the desynchronization mode in response to the count exceeding a predetermined threshold.

23. The process of claim 22 wherein step d) further comprises comparing the determined coupling interval to the calculated enslavement escape interval for a first number of cardiac cycles, and step e) further comprises providing the predetermined threshold as a percentage of the first number of cardiac cycles analyzed in step d).

24. The process of claim 23 wherein providing the predetermined threshold further comprises providing a percentage of the first number of cardiac cycles analyzed in step d) selected from between 50 and 75%.

25. The process of claim 23 wherein providing the predetermined threshold further comprises providing a percentage of approximately 75% of the first number of cardiac cycles analyzed in step d).

26. The process of claim 22 wherein step d) further comprises comparing the determined coupling interval to the calculated enslavement escape interval for a first number of cardiac cycles, and step e) further comprises providing the predetermined threshold as a number of cycles.

27. The process of claim 26 wherein step e) further comprises providing the predetermined threshold as a number of cycles selected from between 10 and 255 cycles.

28. The process of claim 26 wherein step e) further comprises providing the predetermined threshold as approximately 100 cycles.

29. A control processing system for a cardiac pacemaker having a first operating mode of synchronization of the ventricular stimulation to a sensed atrial rhythm and a second operating mode of desynchronization (FALLBACK) of the ventricular stimulation to the atrial rhythm when the atrial rhythm is too rapid, comprising:

a sensor to detect at least one physiological parameter representative of patient activity;

means for calculating an escape interval of enslavement in response to said sensed physiological parameter, including an algorithm relating said at least one sensed physiological parameter to a corresponding escape interval;

means for sensing atrial events;

means for determining a coupling interval between successive sensed atrial events;

a comparator comparing the determined coupling interval and the calculated enslavement escape interval; and means for changing operation from the first mode to the second mode as a function of said comparison.

30. The processing system of claim 29 wherein said function further comprises a prematurity factor to decrease the calculated enslavement escape interval, wherein the comparator compares the determined coupling interval to the decreased calculated enslavement escape interval.

31. The processing system of claim 30 wherein the prematurity factor further comprises a percentage of the calculated enslavement escape interval.

32. The processing system of claim 31 wherein the prematurity factor further comprises a percentage selected from between 0 and 50%.

33. The processing system of claim 31 wherein the prematurity factor further comprises a percentage of approximately 37.5% of the calculated enslavement escape interval.

34. The processing system of claim 30 wherein the prematurity factor further comprises a programmable duration.

35. The processing system of claim 34 wherein the prematurity factor further comprises a programmable duration selected from between 50 and 300 ms.

36. The processing system of claim 34 wherein the prematurity factor further comprises a programmable duration of approximately 150 ms.

37. The processing system of claim 29 wherein the changing operation means further comprises a counter to count the number of cardiac cycles in which the determined coupling interval is less than the calculated enslavement escape interval, wherein the changing operating means operates in response to the count exceeding a predetermined threshold.

38. The processing system of claim 37 wherein the comparator further comprises means for comparing the determined coupling interval to the calculated enslavement escape interval for a first number of cardiac cycles, and wherein the predetermined threshold is a percentage of the first number of cardiac cycles analyzed.

39. The processing system of claim 38 wherein the predetermined threshold further comprises a percentage of the first number of cardiac cycles analyzed selected from between 50 and 75%.

40. The processing system of claim 38 wherein the predetermined threshold further comprises a percentage of approximately 75% of the first number of cardiac cycles analyzed.

41. The processing system of claim 37 wherein the comparator further comprises means for comparing the determined coupling interval to the calculated enslavement escape interval for a first number of cardiac cycles, and wherein the predetermined threshold further comprises a second number of cycles.

42. The processing system of claim 41 wherein the predetermined threshold is a second number of cycles selected from between 10 and 255 cycles.

43. The processing system of claim 41 wherein the predetermined threshold is approximately 100 cycles.

\* \* \* \* \*